United States Patent [19]

Marples et al.

[11] Patent Number: 5,266,566
[45] Date of Patent: Nov. 30, 1993

[54] METHOD OF TREATING FUNGAL INFECTIONS USING STERODIAL ESTER COMPOUNDS

[75] Inventors: Brian A. Marples; Reginald J. Stretton, both of Loughborough, England

[73] Assignee: British Technology Group Limited, London

[21] Appl. No.: 773,908

[22] PCT Filed: May 4, 1990

[86] PCT No.: PCT/GB90/00699
§ 371 Date: Nov. 4, 1991
§ 102(e) Date: Nov. 4, 1991

[87] PCT Pub. No.: WO90/13298
PCT Pub. Date: Nov. 15, 1990

[30] Foreign Application Priority Data
May 5, 1989 [GB] United Kingdom ............... 8910364

[51] Int. Cl.$^5$ .......................................... A61K 31/56
[52] U.S. Cl. .................................... 514/182; 514/858
[58] Field of Search ............................. 514/182, 858

[56] References Cited
PUBLICATIONS
Berger *Medicinal Chemistry*, p. 75, 1985.

*Primary Examiner*—Frederick E. Waddell
*Assistant Examiner*—Gregory Hook
*Attorney, Agent, or Firm*—Nixon & Vanderhye

[57] ABSTRACT

Compounds of the general formula (2):

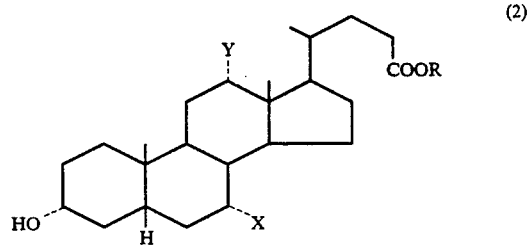

wherein X is a hydrogen atom or a hydroxyl group, Y is a hydrogen atom or a hydroxyl group and R is an alkyl group of 1 to 4 carbon atoms, have anti-fungal activity, especially against organisms selected from Candida spp. and the athlete's foot organism *Trichophyton mentagrophytes* and the ringworm organism *Microsporum audonii*. Further, the compounds wherein X and R are hydrogen atoms and Y is a hydroxyl group (or its non-toxic salts) are useful against *Microsporum audonii*.

4 Claims, No Drawings

METHOD OF TREATING FUNGAL INFECTIONS USING STERODIAL ESTER COMPOUNDS

BACKGROUND OF THE INVENTION

1. Field of the Invention

The invention relates to the anti-fungal use of certain steroids.

2. Description of the Prior Art

UK Patent 2161380 B (National Research Development Corporation) describes the anti-fungal, especially anti-Candida use of, bile acids and derivatives thereof, collectively having the formula

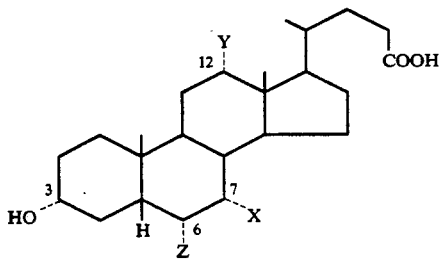

(1)

wherein each of X, Y and Z independently represents a hydrogen atom or a hydroxyl group or a derivative thereof which is a conjugate formed between the carboxyl group and the $NH_2$ group of an amino acid, and their pharmaceutically acceptable salts.

It has been a problem to find alternative anti-fungal compounds having improved therapeutic action against various fungi invasive to the human body.

SUMMARY OF THE INVENTION

It has now been found that compounds of the general formula (2):

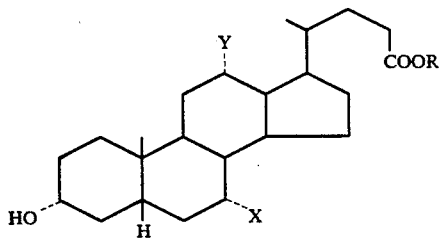

(2)

wherein X is a hydrogen atom or a hydroxyl group, Y is a hydrogen atom or a hydroxyl group and R is an alkyl group of 1 to 4 carbon atoms, have useful anti-fungal activity. Against some fungi, at least, activity appears to be better than is obtainable from the bile salts of the prior patent. Such fungi include Candida species and the fungi implicated in athlete's foot and ringworm (*Trichophyton mentagrophytes* and *Microsporum audonii*). The compounds of the invention are of particular interest for topical application.

The compounds of general formula (2) are mostly known compounds. This invention comprises the specific medical use thereof as anti-fungal agents, said uses to be claimed in the conventional manner appropriate to national patent law. Thus, in particular, the invention, in EPC countries, includes the use of a compound of formula (2) for the manufacture of a medicament for the therapeutic application of treating fungal infections, especially by topical application, while for US purposes it includes a method of treatment of a fungal infection in a human patent, which comprises administering to the patient, preferably topically, a therapeutically effective amount of a compound of formula (2).

Although, as indicated, the anti-fungal use of deoxycholic acid (including its non-toxic salts) is the subject of the said prior patent, the only anti-fungal use specifically described is against Candida. It has now become apparent, from further testing, that deoxycholic acid has a poorer action against Candida (see Table 1 below) compared with the other bile acids of formula (1). On the other hand, it is unexpectedly very highly effective against the *Microsporum audonii* organism implicated in ringworm. According to a further feature of the invention, therefore, there is provided the use of deoxycholic acid and its non-toxic salts as a topical anti-fungal for treatment of infections of *Microsporum audonii* or for which *M. audonii* is a suspected causative agent, especially ringworm. As for the compounds of formula (2) such use is to be claimed in the manner appropriate to national patent law, especially as indicated above. Whereas in the prior patent the sites of topical application specifically mentioned were the vagina, the throat and other cavities, the present application contemplates in relation to deoxycholic acid primarily uses externally of the body cavities and to the ordinary skin.

DESCRIPTION OF THE PREFERRED EMBODIMENTS

Investigations into the effectiveness of various bile acid derivatives has shown that the compounds of the invention have a greater activity against at least one of the three selected fungal strains than salts of the corresponding bile acids of formula (1). These tests are reported below. They indicate in particular that the following methyl esters of formula (2) are particularly effective against the following organisms:

| | | |
|---|---|---|
| X = H, Y = OH ("deoxycholic") | vs | *Candida albicans* |
| X = OH, Y = OH ("cholic") | vs | *Trichophyton mentagrophytes* and *Microsporum audonii* |

While only the methyl and some n-butyl esters have been tested, it is reasonable to suppose that the ethyl, n-propyl, isopropyl, other n-butyl, isobutyl and t-butyl esters will also be effective.

Methyl cholate and deoxycholate are particularly preferred for athlete's foot/ringworm and Candida respectively.

The compounds of the invention are particularly useful in treating candidiasis and infections by dermatophytes. (Dermatophytes are fungi which cause infections of skin, hair and nails in humans and animals). In particular they are useful against fungi of the genera Trichophyton, especially *Trichophyton mentagrophytes* and *rubrum*, and Microsporum. Dermatophytes have many shared antigenic components.

The anti-fungal compounds of formula (2) can be formulated in any conventional way suitable for topical application, bearing in mind that they are water-insoluble. Thus, they can be formulated, for example, as a capsule, suppository or pessary for intracavital application (to the vagina, urethra or rectum) or a gel, ointment, cream or the like, dusting powder or aerosol spray. A suppository or pessary may contain theobroma oil, glycerinated gelatin or polyethylene glycol, for example, as a carrier which melts at body temperature or dissolves in body fluids. The compound of formula (2) can be formulated as an ointment or cream with an oleaginous or waxy binder. An aqueous phase may be present, to provide a cream. Other forms of formulation include gelatin capsules containing the ingredient in a liquid diluent, mixtures with talc or the like to provide dusting powder and aerosol bombs which comprise the ingredient and an inert propellant. Pessaries can be formulated as controlled release compositions using as excipient a polymeric carrier comprising residues which are cross-linked through urethane groups and which comprise polyethylene oxide, as described in UK Patent Specification 2047093 A (National Research Development Corporation).

A preferred formulation is an ointment or cream containing, say, from 1 to 5 percent by weight of the compound of formula (2) depending on its effectiveness.

For athlete's foot or ringworm formulations it could be advisable to include dodecyl sulphate in the product. On testing, this had activity against *M. audonii* and *T. mentagrophytes* and was at least additive in activity with bile salts.

A particularly preferred aspect of the invention comprises the compound of formula (2) in association with deoxycholic acid (or its non-toxic salts) or with an anti-inflammatory agent, especially of the steroidal type, most especially a corticosteroid, e.g. betamethasone, fluocinolone acetonide, beclomethasone dipropionate, hydrocortisone, cortisone or cortisol. These compositions are useful for the treatment of fungal infections of the skin.

A reasonable prediction from the information available is that the invention would be particularly useful in treating the same kinds of topical fungal infections as miconazole.

It is contemplated that the compounds of formula (2) could also be formulated as an aerosol for application to the orapharynx or upper respiratory tract, orally or intranasally. In principle, they could also be administered systemically, e.g. as tablets, pills and capsules for oral ingestion.

Deoxycholic acid (including non toxic salts thereof, especially the sodium salt) can be applied topically by any of the extracavital modes set forth above. The suggestions for formulation are also applicable.

The following tests were carried out. The compounds of formula (1) were tested as the free acids.

TESTS

Organisms

*Candida albicans* NCYC 597; *Trichophyton mentagrophytes* NCPF 224 and *Microsporum audonii* NCPF 638 were used throughout as test organisms. These are open deposits at the National Collection of Yeast Cultures, Norwich UK and the National Collection of Pathogenic Fungi of the Commonwealth Mycological Institute, Kew UK.

Media

All organisms were maintained in a nutrient broth containing (gl$^{-1}$): Lab Lemco (Oxoid), 5; Peptone (Oxoid), 5; NaCl, 10. Cultures for testing antimicrobial activity were grown in this medium for 18 h prior to use. Solidified media were prepared by the addition of Agar (Oxoid No. 3) 1.5% w/v.

Antifungal Activity

Antifungal activity was estimated using solutions of the compound (as the free acid) in dimethyl sulphoxide. A range of concentrations was used for each compound to permit calculation of an approximate MIC. 13 mm discs (Whatman) were soaked in a solution of the appropriate dilution, either allowed to dry, or placed directly onto the surface of nutrient agar plates seeded with the required test organism.

After 24 h incubation the diameters of zones of inhibition were measured. After a further 24 h incubation, the plates were re-examined and zones re-measured. The compounds were tested in three groups.

The results are shown in the following Tables 1 to 3.

TABLE 1

"Group 1" tests for anti-fungal activity

MICs µg/ml

| Basic Skeleton | Formula (1) | Formula (2), R = CH$_3$ |
|---|---|---|
| 3α-OH ("lithocholic", X = H, Y = H) | | |
| *C. albicans* | 410 | |
| *T. ment.* | | |
| *M. aud.* | 100 | |
| 3α, 12α-OH, ("deoxycholic", X = H, Y = OH) | | |
| *C. albicans* | 2100 | 20 |
| *T. ment.* | 300 | 900 |
| *M. aud.* | 30 | 520 |
| 3α, 7α-OH ("chenodeoxycholic", X = OH, Y = H) | | |
| *C. albicans* | 140 | 20* |
| *T. ment.* | 1300 | 460* |
| *M. aud.* | 1000 | 30* |
| 3α,7α, 12α-OH ("cholic", X = OH, Y = OH) | | |
| *C. albicans* | 390 | 3500 |
| *T. ment.* | 10000 | 80 |
| *M. aud.* | 5500 | 50 |

*These three results are discrepant those of "Group 3" in Table 3. Further replication of the tests supports the view that the Group 3 results are the more reliable for methyl chenodeoxycholate.

From the above Table 1 it will be seen that methyl deoxycholate was outstanding against *Candida albicans*, and deoxycholic acid was effective against the ringworm-associated organism, *Microsporum audonii*. Generally, those compounds exhibiting a minimum inhibitory concentration of 100 µg/ml. or less are preferred.

TABLE 2

"Group 2" tests for antifungal activity

MICs µg/ml

| | Candida albicans | Trichophyton mentagrophytes | Microsporum audonii |
|---|---|---|---|
| Methyl lithocholate (2, X = H, Y = H, R = Me) | no effect | 1000 | 950 |
| Butyl lithocholate (2, X = H, Y = H, R = n-Bu) | no effect | 1100 | 900 |
| Methyl deoxycholate (2, X = H, Y = OH, R = Me) | 31 | 250 | 200 |
| Butyl deoxycholate (2, X = H, Y = OH, R = n-Bu) | no effect | 850 | 875 |
| Cholic acid | 405 | ca. 10000 | ca. 5000 |

TABLE 2-continued

"Group 2" tests for antifungal activity

| | MICs μg/ml | | |
|---|---|---|---|
| | Candida albicans | Trichophyton mentagrophytes | Microsporum audonii |
| (1, X = OH, Y = OH) Deoxycholic acid | 2000 | 310 | 35 |
| (1, X = H, Y = OH) DMSO discs (control) | no effect | no effect | no effect |

From the above Table 2 it will be seen that methyl deoxycholate was again highly effective against *C. albicans*. Its effect was not homogeneous: there were many colonies in the zone which were resistant to it. Again, deoxycholic acid was very effective against *M. audonii*.

TABLE 3

"Group 3" tests for anti-fungal activity

| | MICs μg/ml | | |
|---|---|---|---|
| | C. albicans | T. ment. | M. aud. |
| Methyl deoxycholate (2, X = H, Y = OH, R = Me) | 28 | 500 | 450 |
| Methyl chenodeoxycholate (2, X = OH, Y = H, R = Me) | 1000 | 1000 | 800 |
| Butyl chenodeoxycholate (2, X = OH, Y = H, R = n-Bu) | no effect | 1500 | 1000 |
| Deoxycholic acid (1, X = H, Y = OH) | 1800 | 250 | 40 |

Table 3 confirms Tables 1 and 2 in relation to methyl deoxycholate and deoxycholic acid.

The following Examples illustrate the preparation of compounds of the invention.

PREPARATION OF THE METHYL ESTERS

1. Preparation of methyl lithicholate

Lithocholic acid (3g, 7.98 mmoles) in THF (50 ml) was treated dropwise with diazomethane, until the yellow colour persisted. After 25 minutes at 0° C. the solvent was evaporated to yield a brown oil, which on standing began to solidify to yield a light brown solid. The crude product was recrystallised twice from aqueous methanol to afford white granular crystals (2.91 g, 93%), m.p. 123.0°-125.4° C.; IR (nujol mull) 3390 (OH), 1740 (C=O) cm$^{-1}$; $^1$H NMR (250 MHz, CDCl$_3$, TMS) δ0.64 (3H, s, 18-CH$_3$), 0.92 (3H, s, 19-CH$_3$), 3.58-3.66 (1H, m, 3β-H) and 3.66 (3H, s, OCH$_3$). However gas chromatography showed the product to be only 94% pure (for GC procedure see below). From this partially pure product 0.5 g was used for the next step and 1.9 g was further purified by column chromatography on silica gel, eluted with petroleum ether (b.p. 40°/60° C.) and ethyl acetate (1:1) and then recrystallised from petroleum ether (b.p. 40°/60° C.) and ethyl acetate to give pure white crystals of methyl lithocholate (1.8 g), m.p. 123.0°-125.4° C., [α]$_D$+27° (CHCl$_3$, 1%), (Lit.[4] 125.0°-127.5° C., [α]$_D$+22° (CHCl$_3$)), IR (nujol mull) 3308 (OH), 1744 (C=O) cm$^{-1}$; $^1$H NMR (250 MHz, CDCl$_3$, TMS) δ0.64 (3H, s, 18-CH$_3$), 0.92 (3H, s, 19-CH$_3$), 3.58-3.66 (1H, m, 3β-OH) and 3.66 (3H, s, OCH$_3$); $^{13}$C NMR (62.8 MHz, CDCl$_3$, TMS) δ12.04 (C-18), 18.27 (C-21), 23.41 (C-19), 34.59 (C-10), 51.43 (OCH$_3$), 42.74 (C-13), 71.63 (C-3) and 174.72 (C-24).

Gas chromatography on methyl lithocholate showed the compound to be ≧99% pure. (GC procedure: the methyl ester (10 mg) was dissolved in pyridine (1.0 ml) and treated with hexamethyldisilazane (0.2 ml) and trimethylchlorosilane (0.1 ml); 0.3 μl of this solution was injected onto BP-1 column—25 m×0.2 mm at 278° C. Retention time=13.4 minutes). This compound was submitted for testing (Group 2).

2. Preparation of methyl deoxycholate

Deoxycholic acid (0.54 g, 1.4 mmol) in THF (10 ml) at 0° C. was treated dropwise with freshly prepared diazomethane in ether (prepared in the usual manner from diazald) until the yellow colour persisted. After 15 minutes at 0° C. the solvent was evaporated to yield a white foam (0.60 g). The compound would not recrystallise, although gas chromatography showed the product to be 99% pure. The product was further purified by preparative silica tlc. (solvent system: EtOAc/CH$_2$Cl$_2$/AcOH—10:10:1) to afford pure methyl deoxycholate[2] (0.45 g, 80%) as a foam: $^1$H NMR (60 MHz; CDCl$_3$) δ0.67 (3H, s, 18-CH$_3$), 0.92 (3H, s, 18-CH$_3$), 2.18 (2H, s [exchanges on adding D$_2$O], 3α and 12α OH's), 3.2-3.7 (1H; m. 3β-H), 3.65 (3H, s, —OMe), 3.8-4-1 (1H, m, 12β-H); IR (nujol mull) 3368 (OH's), 1740 (C=O) cm$^{-1}$; MS: Found m/z 388.2951; C$_{25}$H$_{40}$O$_3$(M-H$_2$O) requires 388.2977.

The methyl deoxycholate was submitted for testing (Group 1) without further purification.

The above preparation was repeated, yielding on evaporation of the solvent, a colourless glass. A portion of this was used to prepare the corresponding n-butyl ester (see below) and another portion was further purified by column chromatography on silica gel, eluting with petroleum ether (b.p. 40°/60° C.) and ethyl acetate (1:1) to give a pure colourless glass of compound, [α]$_D$ +37° (CHCl$_3$, 1%) (lit.[2] m.p. 105°-160° C., [α]$_D$ +48° (MEK)); IR (CHCl$_3$) 3604, 3444 (OH), 1728 (C=O) cm$^{-1}$; $^1$H NMR (250 MHz, CDCl$_3$, TMS) δ0.68 (3H, s, 18-CH$_3$), 0.91 (3H, s, 19-CH$_3$), 3.58 (1H, m, 3β-H), 3.66 (3H, s, OCH$_3$) and 3.98 (1H, m, 12β-H), $^{13}$C NMR (62.8 MHz, CDCl$_3$, TMS) δ12.76 (C-18), 17.76 (C-21), 23.17 (C-19), 35.20 (C-10), 47.34 (C-13), 51.47 (OCH$_3$), 71.78 (C-3), 73.15 (C-12), and 174.70 (C-24). Gas chromatography (see Example 1) showed the product to be ≧99% pure, retention time +14.4 minutes. This compound was submitted for testing (Groups 2 and 3).

3. Preparation of methyl chenodeoxycholate

Chenodeoxycholic acid (0.5 g, 1.3 mmol) in THF (10 ml) at 0° C. was treated dropwise with freshly prepared diazomethane in ether (prepared in the usual manner from diazald) until the yellow colour persisted. After 15 minutes at 0° C. the solvent was evaporated to yield a white foam (0.55 g). The compound would not recrystallise, although gas chromatography showed the product to be 97% pure. The product was further purified by preparative silica tlc. (solvent system: EtOAc/CH$_2$Cl$_2$/AcOH—10:10:1) to afford pure methyl chenodeoxycholate[3] (0.42 g, 81%) as a foam: $^1$H NMR (60 MHz; CDCl$_3$) δ0.65 (3H, s, 18-CH$_3$), 0.91 (3H, s, 19-CH$_3$), 1.85 (2H, s [exchanges on adding D$_2$O], 3α and 7α OH's), 3.1-3.7 (1H, m, 3β-H), 3.64 (3H, s, —OMe), 3.7-3.9 (1H, m, 7β-H); IR (nujol mull) 3384 (OH's), 1740 (C=O) cm$^{-1}$; MS: Found m/z 406.3077; C$_{25}$H$_{42}$O$_4$(M) requires 406.3083.

The methyl chenodeoxycholate was submitted for testing (Group 1) without further purification.

The above preparation was repeated, yielding, on evaporation of the solvent, a colourless glass. A portion of this compound was used to prepare the corresponding n-butyl ester (see below) and another portion was purified using column chromatography on silica gel, eluting with petroleum ether (b.p. 40°/60° C.) and ethyl acetate (1:1) to afford methyl chenodeoxycholate as a colourless glass (0.298 g), $[\alpha]_D$ +22° (CHCl$_3$, 1%), IR (CHCl$_3$) 3600, 3440 (OH), 1730 (C=O) cm$^{-1}$; $^1$H NMR (250 MHz, CDCl$_3$, TMS), δ0.66 (3H, s, 18-CH$_3$), 0.91 (3H, s, 19-CH$_3$), 3.46 (1H, m, 3β-H), 3.66 (3H, s, OCH$_3$), and 3.85 (1H, m, 7β-H); $^{13}$C NMR (62.8 MHz, CDCl$_3$, TMS) δ11.80 (C-18), 18.29 (C-21), 22.80 (C-19), 34.65 (C-10), 39.46 (C-13), 51.49 (OCH$_3$), 68.55 (C-3), 72.03 (C-7), and 174.74 (C-24). Gas chromatography (see Example 1) showed the product to be ≧99% pure, retention time = 16 minutes. This compound was submitted for testing (Group 3).

4. Preparation of methyl cholate

Cholic acid (1a) (2.0 g, 4.9 mmol) in THF (40 ml) at 0° C. was treated dropwise with freshly prepared diazomethane in ether (prepared in the usual manner from diazald: diazald is N-methyl-N-nitroso-p-toluenesulphonamide) until the yellow colour persisted. After 15 minutes at 0° C. the solvent was evaporated to yield a white foam (2.1 g, 100%). Recrystallisation from methanol afforded pure methyl cholate[1] (1.3 g, 63%): m.p. 158°-159° C. (crystals began to melt 86°-88° C. and then resolidified—this was probably due to the retention of methanol in the crystals, see NMR data) [Lit[1] 156°-158° C.]; $^1$H NMR (60 MHz; CDCl$_3$) δ0.66 (3H, s, 18-CH$_3$), 0.87 (3H, s, 19-CH$_3$), 3.0-3.6 (1H, m. 3β-H), 3.2-3.5 (3H, m [exchanges on adding D$_2$O], 3α, 7α and 12α OH's), 3.48 (s, MeOH of crystallisation [ca. 1 mol equiv.]), 3.65 (3H, s, 24-OMe), 3.7-3.9 (1H, m, 7β-H), 3.8-4.0 (1H, m, 12β-H); IR (nujol mull) 3392, 3300 (OH's), 1734 (C=O) cm$^{-1}$.

The methyl cholate was submitted for testing (Group 1) without any further purification, since gas chromatography showed the product to be 96% pure.

PREPARATION OF THE NORMAL BUTYL ESTERS

5. Preparation of n-butyl lithocholate

Ester exchange was achieved by refluxing the methyl lithocholate (0.5 g, 1.28 mmoles) in an excess of butan-1-ol (50 ml) and conc. HCl (1.5 ml) for 1¼ h. The reaction mixture was cooled and the solvent removed under vacuum to afford an off white gum. The crude product was chromatographed on a silica gel column, eluting with petroleum ether (b.p. 40°/60° C.) and ethyl acetate (1:1) to give a white solid (0.394 g, 71%). This white solid was further purified by recrystallising twice first from aqueous methanol and then from aqueous methanol and acetone to give white granular crystals of the n-butyl lithocholate (0.369 g, 66%), m.p. 82.1°-83.9° C.; $[\alpha]_D$ +21° (CHCl$_3$, 1.05%); IR (nujol mull) 3316 (OH), 1740 (C=O) cm$^{-1}$; $^1$H NMR (250 MHz, CDCl$_3$, TMS) δ0.64 (3H, s, 18-CH$_3$), 0.90 (3H, s, 19-CH$_3$), 0.92 (3H, t, J 6.8 Hz, δ-CH$_3$), 3.56-3.70 (1H, m, 3β-H) and 4.06 (2H, t, J 6.8 Hz, OCH$_2$); $^{13}$C NMR (62.8 MHz, CDCl$_3$, TMS) δ12.06 (C-18), 13.73 (δ-CH$_3$), 16.28 (C-21), 19.16 (γ-CH$_2$), 23.40 (C-19), 30.60-31.37 (C-2, C-22, C-23, β-CH$_2$), 34.61 (C-10), 42.78 (C-13), 64.14 (OCH$_2$), 71.68 (C-3), and 174.77 (C-24); C$_{28}$H$_{48}$O$_3$ requires C, 77.71; H, 11.19% found C, 77.51; H, 11.34%; MS: requires M 432, (positive ion plasma spray); found M+NH$_4$+ 450. Gas chromatography (as in Example 1) showed the product to be ≧99% pure, retention time = 21.2 minutes. This compound was submitted for testing (Group 1).

6. Preparation of n-butyl deoxycholate

Ester exchange was achieved by refluxing the methyl deoxycholate (colourless glass, 0.5 g, 1.23 mmoles) in an excess of butan-1-ol (50 ml) and conc. HCl (1.5 ml) for 1 h. The reaction mixture was cooled and the solvent removed under vacuum to yield a yellow oil. The crude product was chromatographed on a column of silica gel, eluting with petroleum ether (b.p. 40°/60° C.): ethyl acetate (1:1) to yield a white solid (0.422 g, 77%). Attempts to recrystallise the solid from aqueous methanol and acetone produced only oils. To further purify the product a sample (0.17 g) was chromatographed on silica gel, eluted with petroleum ether (b.p. 40°/60° C.) and ethyl acetate (1:1), to yield a colourless glass of n-butyl deoxycholate (0.16 g), $[\alpha]_D$ +33° (CHCl$_3$, 1%); IR (CHCl$_3$) 3596, 3456 (OH), 1722 (C=O) cm$^{-1}$; $^1$H NMR (250 MHz, CDCl$_3$, TMS) δ0.68 (3H, s, 18-CH$_3$), 0.91 (3H, s, 19-CH$_3$), 0.96 (3H, t, J 6.7 Hz, δ-CH$_3$), 3.57-3.66 (1H, m, 3β-H), 3.98 (1H, m, 12β-H) and 4.06 (2H, t, J 6 6.7 Hz, OCH$_2$); $^{13}$C NMR (62.8 MHz, CDCl$_3$ TMS) δ12.06 (C-18), 13.72 (δ-CH$_3$), 17.33 (C-21), 19.20 (γ-CH$_2$), 23.16 (C-19), 30.55-31.39 (C-2, C-22, C-23, β-CH$_2$), 34.15 (C-10), 46.55 (C-13), 64.16 (OCH$_2$), 71.63 (C-3), 73.18 (C-12) and 174.36 (C-24); C$_{28}$H$_{48}$O$_4$ requires C, 74.94 H, 10.79%; found C, 74.80 H, 10.72% ; MS: requires M 448 (positive ion plasma spray); found M+NH$_4$+ 466. Gas chromatography (as in Example 1) showed the product to be ≧99% pure, retention time = 25 minutes. This compound was submitted for testing (Group 2).

7. Preparation of n-butyl chenodeoxycholate

Ester exchange was achieved by refluxing the methyl chenodeoxycholate (colourless glass, 0.5 g, 1.27 mmoles) in an excess of butan-1-ol (50 ml) and conc. HCl (1.5 ml) for 1 h. The reaction mixture was cooled and the solvent removed under vacuum to afford a colourless gum (0.482 g, 87%). A sample of the product was purified using column chromatography on silica gel, eluting with petroleum ether (b.p. 40°/60° C.) and ethyl acetate (1:1) to give a pure colourless glass of n-butyl chenodeoxycholate, (0.21 g), $[\alpha]_D$+18° (CHCl$_3$, 1%); IR (CHCl$_3$) 3600, 3430 (OH), 1720 (C=O) cm$^{-1}$; $^1$H NMR (250 MHz, CDCl$_3$, TMS) δ0.66 (3H, s, 18-CH$_3$), 0.91 (3H, s, 19-CH$_3$) 0.93 (3H, t, J 6.4 Hz, δ-CH$_3$), 3.46 (1H, m, 3β-H), 3.85 (1H, m, 7β-H), 4.06 (2H, t, J 6.9 Hz, OCH$_2$); $^{13}$C NMR (62.8 MHz, CDCl$_3$, TMS) δ11.78 (C-18), 13.73 (δ-CH$_3$), 18.28 (C-21), 19.18 (γ-CH$_2$), 22.80 (C-19), 30.73-31.30 (C-2, C-22, C-23, β-CH$_2$), 35.07 (C-10), 42.72 (C-13), 64.15 (OCH$_2$), 68.54 (C-3), 72.02 (C-7), and 174.60 (C-24); C$_{28}$H$_{48}$O$_3$ requires C, 74.94; H, 10.79% found C, 74.85; H, 10.77%; MS: requires M 448 (positive ion plasma spray); found M+NH$_4$+ 466. Gas chromatography (as in Example 1) showed the product to be ≧98% pure, retention time = 28.1 minutes. This compound was submitted for testing (Group 3).

Literature References

1. Elsevier's Encycloapedia of Organic Chemistry, 1962 14, 3288s
2. Elsevier's Encycloapedia of Organic Chemistry, 1962 14, 3229s
3. A. F. Hofmann, Acta Chem. Scand. 1963, 17, 173.
4. Elsevier's Encyclopaedia of Organic Chemistry, 1962 14, 3095s

We claim:
1. A method of treating a fungal infection in a human patient which comprises administering topically to the patient a therapeutically effective amount of a compound of formula (2):

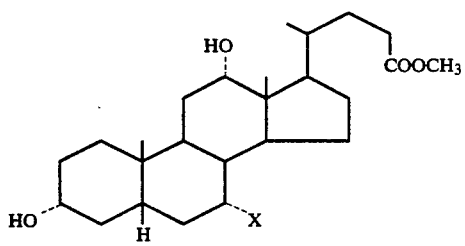

(2)

wherein X is hydrogen or hydroxyl, subject to a condition selected from the group consisting of (a) and (b) as follows:
  (a) X is hydrogen and the infection is by a fungus of the Candida genus; and
  (b) X is hydroxyl and the infection is by a fungus of the Microsporum or Trichophyton genus.

2. The method of claim 1 wherein the infection by the fungus of the Candida genus is vaginal.

3. The method of claim 1 wherein the infection by the fungus of the Microsporum genus is ringworm.

4. The method of claim 1 wherein the infection by the Trichophyton genus is ringworm or athlete's foot.

* * * * *